US010299739B2

(12) United States Patent
Watanabe (10) Patent No.: US 10,299,739 B2
(45) Date of Patent: May 28, 2019

(54) MEDICAL MONITORING APPARATUS (71) Applicant: OLYMPUS CORPORATION, Tokyo (JP)

(72) Inventor: Nobuyuki Watanabe, Yokohama (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 15/833,449

(22) Filed: Dec. 6, 2017

(65) Prior Publication Data
US 2018/0153482 A1 Jun. 7, 2018

Related U.S. Application Data (63) Continuation of application No. PCT/JP2016/086007, filed on Dec. 5, 2016.

(51) Int. Cl.
G08B 21/02 (2006.01)
A61B 5/00 (2006.01)
(Continued)

(52) U.S. Cl.
CPC .......... A61B 5/746 (2013.01); A61B 5/02055 (2013.01); A61B 5/0402 (2013.01);
(Continued)

(58) Field of Classification Search
CPC ....... A61B 5/087; A61B 5/412; A61B 5/4818; A61B 5/726; A61B 5/0205;
(Continued)

(56) References Cited

U.S. PATENT DOCUMENTS

2007/0060872 A1* 3/2007 Hall ................... A61B 5/14546
604/66
2008/0071177 A1* 3/2008 Yanagidaira ........... A61B 5/024
600/483
(Continued)

FOREIGN PATENT DOCUMENTS

JP 2008-237686 A 10/2008
JP 2015-042293 A 3/2015
WO WO 2005/055824 A1 6/2005

OTHER PUBLICATIONS

PCT/ISA/210 issued in PCT/JP2016/086007, dated Feb. 21, 2017.
Written opinion of the ISA of PCT/JP2016/086007, dated Feb. 21, 2017 (with partial English translation).

Primary Examiner — Daniel Previl
(74) Attorney, Agent, or Firm — Greer Burns & Crain, Ltd.

(57) ABSTRACT

A medical monitoring apparatus that monitors a status of a patient according to biological information of the patient includes a reliability evaluator 510 configured to obtain first biological information measured by a bedside monitor 200 and second biological information measured by a wearable sensor 300, and to evaluate a reliability of the second biological information according to a correlation between the first biological information and the second biological information, the first biological information and the second biological information belonging to an identical measurement item, and an alert determinator 600 configured to determine, using the first biological information and the second biological information, whether to issue an alert about an abnormality under a condition that depends on the reliability.

11 Claims, 9 Drawing Sheets (51) Int. Cl.
*G16H 40/67* (2018.01)
*G16H 40/63* (2018.01)
*A61B 5/0402* (2006.01)
*A61B 5/0476* (2006.01)
*A61B 5/0205* (2006.01)
*G16H 40/20* (2018.01)
*A61B 5/024* (2006.01)
*A61B 5/021* (2006.01)

(52) U.S. Cl.
CPC .......... *A61B 5/0476* (2013.01); *A61B 5/7221* (2013.01); *A61B 5/742* (2013.01); *A61B 5/7405* (2013.01); *G16H 40/20* (2018.01); *G16H 40/63* (2018.01); *G16H 40/67* (2018.01); *A61B 5/021* (2013.01); *A61B 5/02438* (2013.01); *A61B 5/7246* (2013.01); *A61B 5/7282* (2013.01)

(58) Field of Classification Search
CPC ... A61B 5/14551; A61B 5/0836; A61B 5/145; A61B 7/003; A61B 5/00; A61B 5/0024; A61B 5/01; A61B 5/0476; A61B 5/7282; A61B 5/742

USPC .......... 340/573.1, 870.07, 566, 568.1, 568.2, 340/572.1, 582, 601, 614, 683, 691.6, 340/692, 3.1, 5.32, 5.82, 7.58, 7.61, 7.62, 340/825.52

See application file for complete search history.

(56) References Cited

U.S. PATENT DOCUMENTS

| | | | |
|---|---|---|---|
| 2013/0066395 A1* | 3/2013 | Simon | A61N 2/006 607/48 |
| 2013/0116578 A1* | 5/2013 | An | A61B 5/0205 600/484 |
| 2015/0057554 A1* | 2/2015 | Watson | A61B 5/02125 600/485 |
| 2015/0205931 A1* | 7/2015 | Wang | G16H 40/63 702/19 |
| 2016/0199007 A1* | 7/2016 | Kudo | A61B 5/7221 340/870.07 |
| 2018/0055386 A1* | 3/2018 | Zielinski | A61B 5/0002 |

* cited by examiner

| CORRELATION | LEVEL OF RELIABILITY |
|---|---|
| 70% OR LOWER | 1 |
| 70~80% | 2 |
| 80% OR HIGHER | 3 |

F I G. 5 A

| CORRELATION | LEVEL OF RELIABILITY |
|---|---|
| 50% OR LOWER | 1 |
| 50~90% | 2 |
| 90% OR HIGHER | 3 |

MEDICAL MONITORING APPARATUS

CROSS-REFERENCE TO RELATED APPLICATIONS

This application is a Continuation application of PCT Application No. PCT/JP2016/86007, filed Dec. 5, 2016, the entire contents of all of which are incorporated herein by reference.

BACKGROUND OF THE INVENTION

Field of the Invention

The present invention is related to a medical monitoring apparatus that monitors the status of a patient so as to issue an alert.

Description of the Related Art

In order to monitor the statuses of patients who are under treatment, medical institutions such as hospitals widely employ biological information monitoring apparatuses that comprehensively monitor the biological information of the patients. Such biological information monitoring apparatuses are generally referred to as bedside monitors.

As is suggested by the name, bedside monitors are installed at the bedside of patients in wards, CCUs, ICUs, etc. Doctors, nurses, and other medical staffs obtain biological information such as the heart rate, blood pressure, body temperature, respiratory rate, etc. of a patient through the bedside monitor, and understand the status of that patient. A system is also proposed in which a bedside monitor is connected to a nurse call function so that when an abnormality occurs in the biological information of a patient, an alert is issued in the form of a nurse call (Patent Document 1). [Patent document 1] WO2005/055824

SUMMARY OF THE INVENTION

A medical monitoring apparatus that monitors a status of a patient according to biological information of the patient includes a reliability evaluator configured to obtain first biological information measured by a first measurement apparatus and second biological information measured by a second measurement apparatus, and to evaluate a reliability of the second biological information according to a correlation between the first biological information and the second biological information, the first biological information and the second biological information belonging to an identical measurement item, and an alert determinator configured to determine, using the first biological information and the second biological information, whether to issue an alert about an abnormality under a condition that depends on the reliability.

DESCRIPTION OF THE EMBODIMENTS

Figure 1:
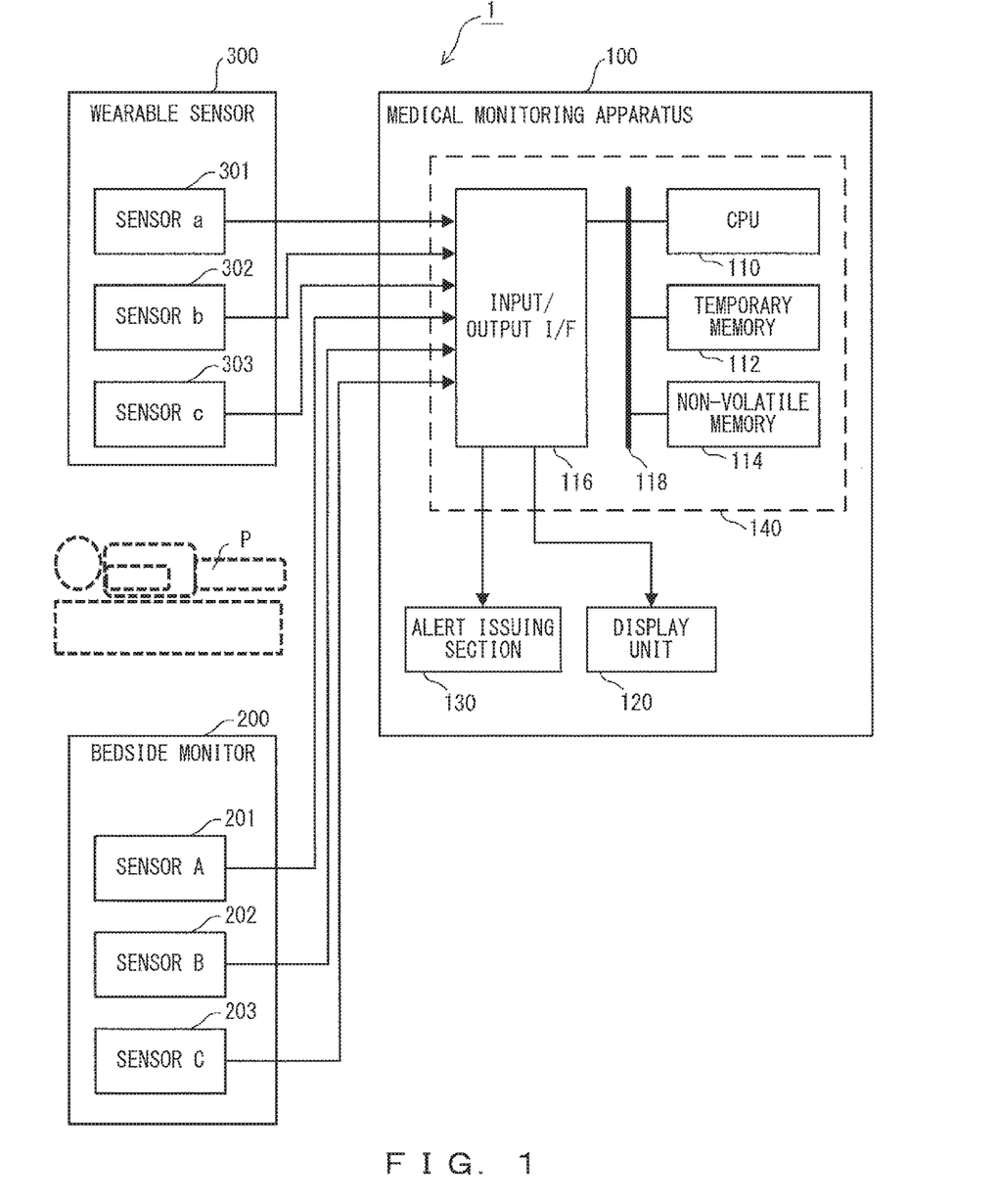
FIG. 1 is a block diagram illustrating a basic configuration example of a medical monitoring system according to the present embodiment.

Hereinafter, explanations will be given for the embodiments of the present invention by referring to the drawings. FIG. 1 is a block diagram illustrating a basic configuration example of a medical monitoring system 1 according to the present embodiment. The medical monitoring system 1 includes a medical monitoring apparatus 100, a bedside monitor 200 and a wearable sensor 300.

The medical monitoring apparatus 100 obtains biological information from sensors (the bedside monitor 200 and the wearable sensor 300) for detecting the status (state) of a patient, and issues an alert to doctors or nurses (medical staff members) when an abnormality occurs in the patient.

The bedside monitor 200 is a main measurement apparatus that measures the biological information of a patient. The bedside monitor 200 will also be referred to as a first measurement apparatus. Biological information detected by the bedside monitor 200 is body temperature, heart rate, blood pressure, irregular pulse, Co2 concentration in blood, EEG (Electroencephalogram) and ECG (Electrocardiogram).

The bedside monitor 200 is provided with a sensor corresponding to each item of biological information (such as body temperature, heart rate, etc.). The sensors of the bedside monitor 200 in principle detect biological information with the patient laid on a bed. The present embodiment describes three sensors: sensor A 201, sensor B 202 and sensor C 203. For example, sensor A 201 is a sensor for detecting body temperatures, sensor B 202 is a sensor for detecting blood pressure, and sensor C 203 is a sensor for detecting heart rates. Also, the bedside monitor 200 may be provided with a monitor device (not illustrated) that displays biological information detected through the respective sensors.

In order to detect the status of a patient accurately, the bedside monitor 200 is generally provided with highly accurate sensors or highly sensitive sensors. However, highly accurate sensors or highly sensitive sensors cause problems as well. For example, the high sensitivity of a sensor for measuring heart rates may lead to a case where a change accompanying ambient vibrations or movements of a patient is falsely detected as a change in the heart rate. Similarly, highly sensitive electrocardiogram sensors tend to pick up signals accompanying ambient radio waves, ambient electric noise and movements of patients.

Because various factors may also cause false detection in the bedside monitor 200 as described above, determinations of abnormalities of patients based on information from the bedside monitor 200 alone would lead to the inclusion of false alerts.

Thus, in order to verify an abnormality of a patient detected by the bedside monitor 200, the present embodiment utilizes a sensor that is for the same measurement target as that of a sensor in the bedside monitor 200 and that has a measurement principle, measurement accuracy or an attaching position that is different from the sensor in the bedside monitor 200. This sensor having a different measurement principle, measurement accuracy or attaching position will also be referred to as a second measurement apparatus.

The present embodiment uses a wearable sensor as a second measurement apparatus. The wearable sensor 300 is a general term for sensors that are attached directly to the body of a patient so as to detect various types of biological information of the patient. The wearable sensor 300 is a second measurement apparatus for preventing false issuance of alerts that is based on biological information detected by the respective sensors in the bedside monitor 200.

The wearable sensor 300 can also be considered to be a sensor of a size that is small enough to allow the patient to move while wearing it. The wearable sensor 300 is for example a wristwatch-type sensor to be attached to wrists.

As described above, sensors that detect biological information belonging to measurement items identical to those of the respective sensors of the bedside monitor 200 are provided as the wearable sensor 300. Sensor a 301, sensor b 302 and sensor c 303 in the wearable sensor 300 have measurement items that are identical to those of sensor A 201, sensor B 202 and sensor C 203 of the bedside monitor 200.

For example, sensor A 201 is a thermistor-type thermometer, and sensor a 301 is an infrared thermometer. Also, sensor C 203 is a sensor that measures heart rate by being attached to the chest, and sensor c 303 is a sensor that measures heart rate by being worn on the wrist. Note that biological information measured by the bedside monitor 200 will be referred to as first biological information and biological information measured by the wearable sensor 300 will be referred to as second biological information hereinafter.

The medical monitoring apparatus 100 includes a CPU (Central Processing Unit) 110, a temporary memory 112, a non-volatile memory 114, an input/output I/F (interface) 116, a bus 118, a display unit 120 and an alert issuing section 130.

The CPU 110 reads a control program from the non-volatile memory 114, and comprehensively controls the medical monitoring apparatus 110 through a software process in accordance with the read control program. The temporary memory 112, the non-volatile memory 114 and the input/output I/F 116 are connected to the CPU 110 via the bus 118.

The temporary memory 112 temporarily stores a control program and various types of data. The temporary memory 112 is for example a DRAM (Dynamic Random Access Memory). The non-volatile memory 114 stores a control program, various types of tables, and reliability data, which will be described later, etc. The non-volatile memory 114 is for example an HDD (Hard Disk Drive) or a flash memory.

The input/output I/F 116 controls sensor A 201 etc. of the bedside monitor 200, sensor a 301 etc. of the wearable sensor 300, and input/output with external devices. Biological information output from the bedside monitor 200 or the wearable sensor 300 is input to the medical monitoring apparatus 100 via the input/output I/F 116.

Also, the input/output I/F 116 is connected to the display unit 120 and the alert issuing section 130. The display unit 120 displays biological information obtained by the sensors or information etc. of correlations and reliabilities, which will be described later. Note that the CPU 110, the temporary memory 112, the non-volatile memory 114, the input/output I/F 116 and the bus 118 may be units of an information processing apparatus 140 such as a personal computer.

The alert issuing section 130 is a speaker that reports an abnormality of a patient to a medical staff member such as a doctor, a nurse or other medical staff members. The alert issuing section 130 may include a display device that displays an alert window. A speaker or a display device serving as the alert issuing section 130 may be of for example a stationary type that is to be set in a nurse station or may be of for example a portable type that is carried by a doctor or a nurse.

Figure 2:
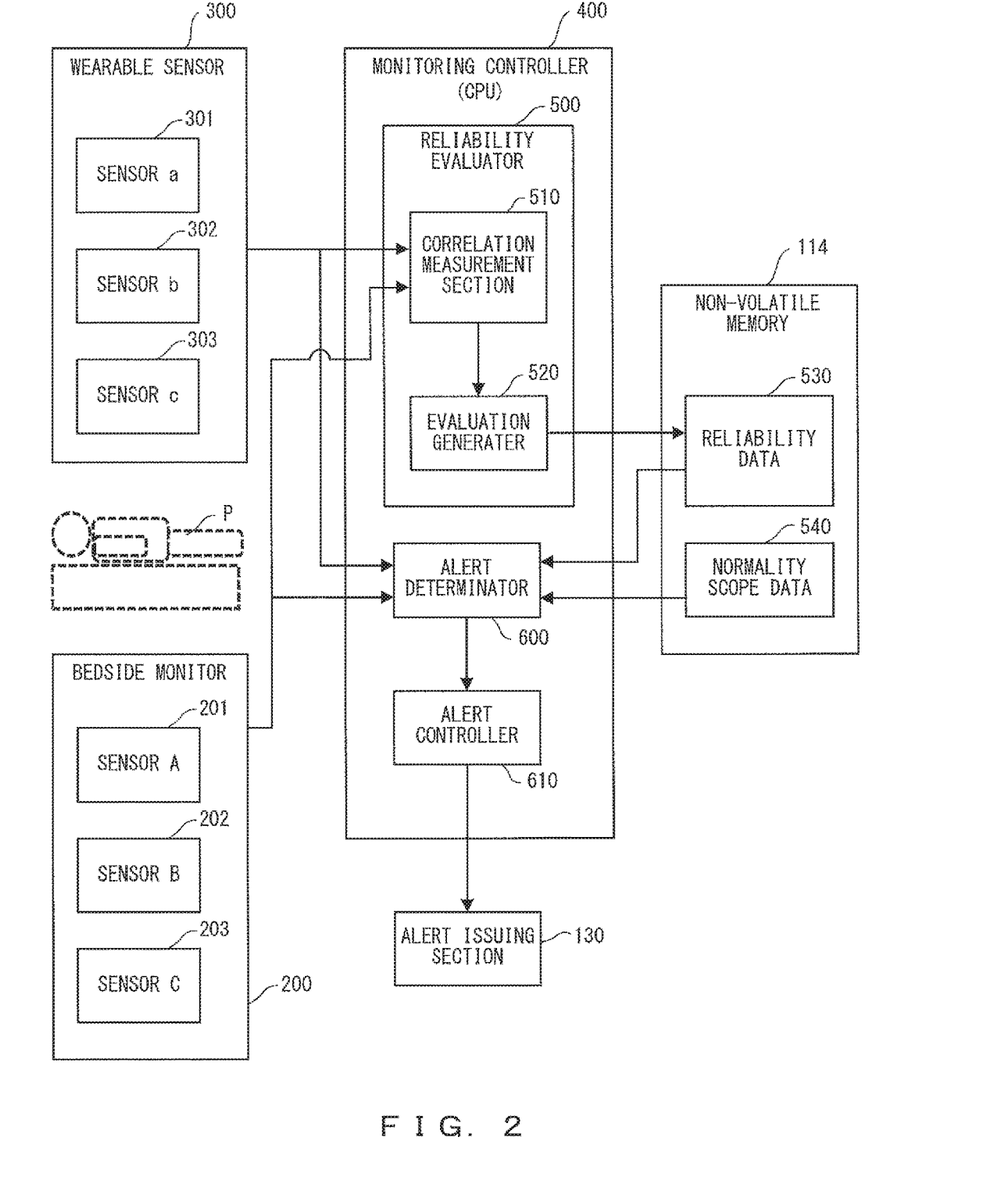
FIG. 2 is a functional block diagram of an alert determination process performed by the medical monitoring system.

FIG. 2 is a functional block diagram of a monitoring process performed by the medical monitoring system 1. A monitoring controller 400 performs a monitoring process, and is implemented by a software process performed by the CPU that has read a control program. The monitoring controller 400 includes a reliability evaluator 500, an alert determinator 600 and an alert controller 610.

The reliability evaluator 500 evaluates the reliability of biological information of the wearable sensor 300, and generates reliability data 530. The reliability data 530 is data used for making a determination about an alert performed by the alert determinator 600 when an abnormality is detected in the biological information during the monitoring of the status of a patient.

The reliability evaluator 500 obtains first biological information and second biological information, and evaluates the reliability of the biological information of the wearable sensor 300 on the basis of a correlation between the two pieces of biological information.

The reliability evaluator 500 includes a correlation measurement section 510 and an evaluation generator 520. The correlation measurement section 510 measures a correlation between first biological information and second biological information that belong to an identical measurement item. In other words, the correlation measurement section 510 measures correlations respectively for data between sensor A and sensor a, data between sensor B and sensor b, and data between sensor C and sensor c.

Also, the evaluation generator 520 generates the reliability data 530 of the second biological information from the correlation between the first biological information and the second biological information measured by the correlation measurement section 510. The reliability data 530 generates reliability data respectively for sensors (sensor a, sensor b and sensor c).

The evaluation generator 520 stores the generated reliability data in the non-volatile memory 114. Note that the reliability evaluator 500 evaluates a reliability and stores the reliability data prior to the monitoring of a patient. Also, the reliability evaluator 500 measures a correlation so as to generate latest reliability data on an as-needed basis or at prescribed timings (once per day for example) during the monitoring. It is suitable that reliability data be updated to latest versions on an as-needed basis.

The alert determinator 600 uses first biological information and second biological information to determine whether to issue an alert about an abnormality under a condition that depends upon reliability data. First, the alert determinator 600 determines whether an abnormality occurred in the first biological information of any of sensor A 201 and other sensors. The alert determinator 600 makes a determination about the occurrence of an abnormality by comparing normality scope data 540 of sensor A 201 and other sensors of the bedside monitor 200 and the first biological information, the normality scope data 540 being stored in the non-volatile memory 114 in advance. When it is determined that an abnormality has occurred in any of the pieces of the first biological information, the alert determinator 600 determines whether to issue an alert about the abnormality on the basis of the second biological information belonging to the identical measurement item and the reliability data 530 of that second biological information. Hereafter, the second biological information belonging to an identical item will also be referred to as "corresponding second biological information".

Then, the alert determinator 600 makes a determination of an alert in accordance with the level of the reliability data 530 of the corresponding second biological information. Also, the alert determinator 600 may set different alarm sounds depending upon the reliability data 530 of the second biological information for which an alert determination was made. This will be described in more detail later.

When the alert determinator 600 determines that an alert is to be issued, the alert controller 610 controls the alert issuing section 130 so as to make it generate an alarm sound.

Figure 3:
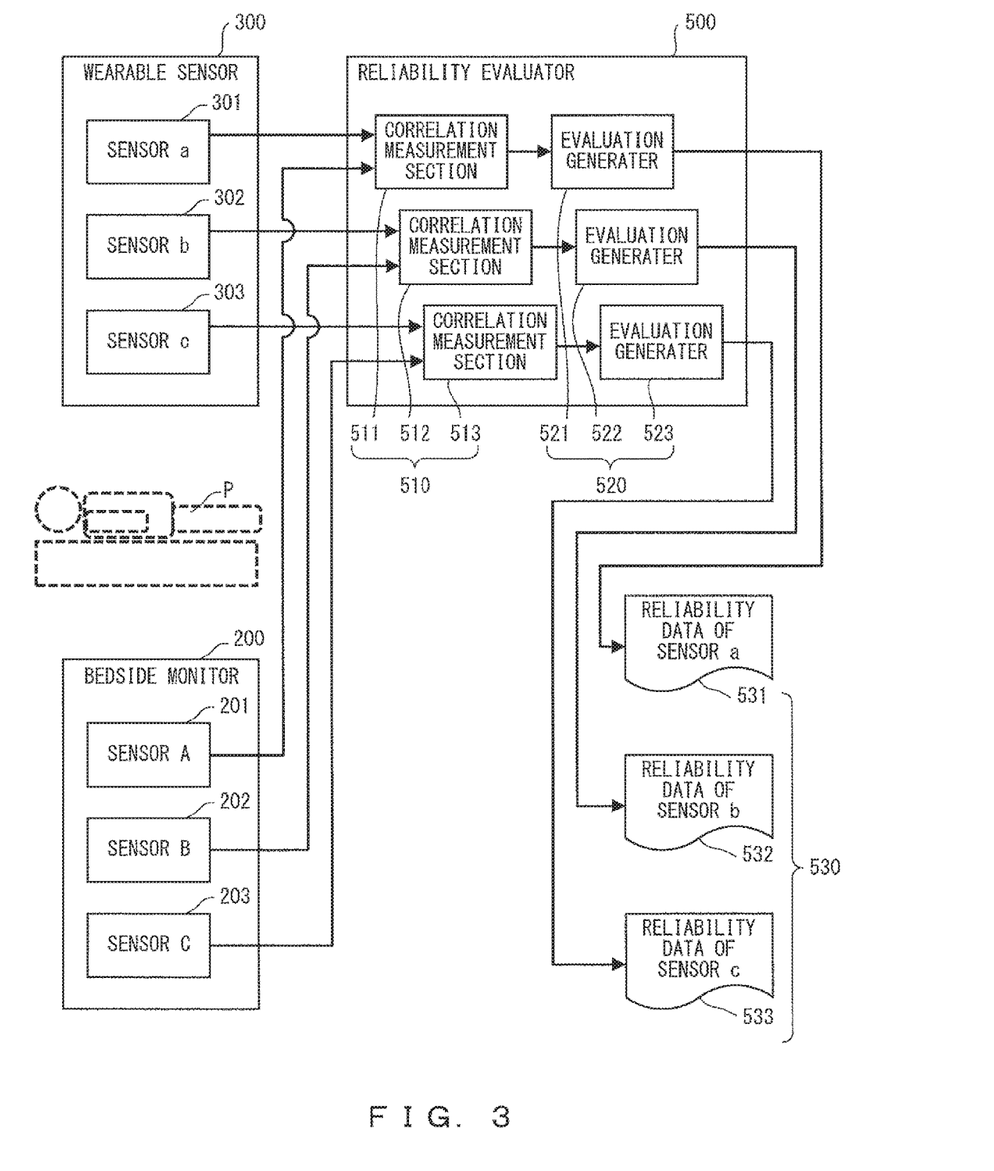
FIG. 3 is a block diagram of a process of generating reliability data.
Figure 4:
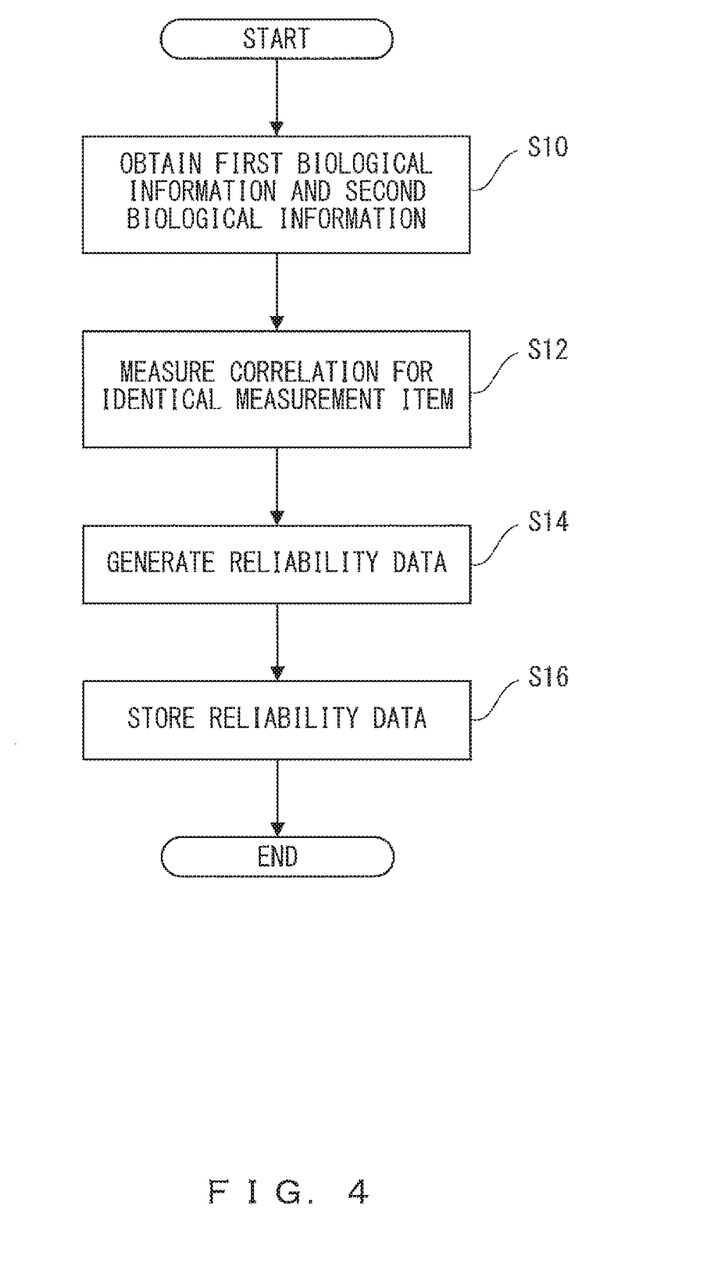
FIG. 4 is a flowchart explaining the sequence of a process of generating reliability data.

Next, explanations will be given for a process that is performed by the aforementioned evaluation generator 520 for generating reliability data. FIG. 3 is a block diagram of a process of generating reliability data. FIG. 4 is a flowchart explaining the sequence of a process of generating reliability data.

As illustrated in FIG. 3, the reliability evaluator 500 includes correlation measurement sections 511, 512 and 513 as the correlation measurement section 510. The correlation measurement section 511 measures a correlation of data between sensor A and sensor a. The correlation measurement section 512 measures a correlation of data between sensor B and sensor b. The correlation measurement section 513 measures a correlation of data between sensor C and sensor c.

Also, the reliability evaluator 500 includes evaluation generators 521, 522 and 523 as the evaluation generator 520. The evaluation generator 521 generates reliability data 531 of sensor a on the basis of the correlation measured by the correlation measurement section 511. Similarly, the evaluation generator 522 generates reliability data 532 of sensor b on the basis of the correlation measured by the correlation measurement section 512. Similarly, the evaluation generator 523 generates reliability data 533 of sensor c on the basis of the correlation measured by the correlation measurement section 513.

By referring to FIG. 4, explanations will be given for the sequence of a process of generating reliability data. Note as described above that the process of generating reliability data is a process performed prior to the actual monitoring of the status of a patient. The reliability evaluator 500 obtains first biological information and second biological information (step S10). The correlation measurement section 510 measures correlations between the first biological information and the second biological information for identical measurement items (step S12).

The evaluation generator 520 generates the reliability data 530 of the second biological information from the respective measured correlations (step S14).

Figure 5A:
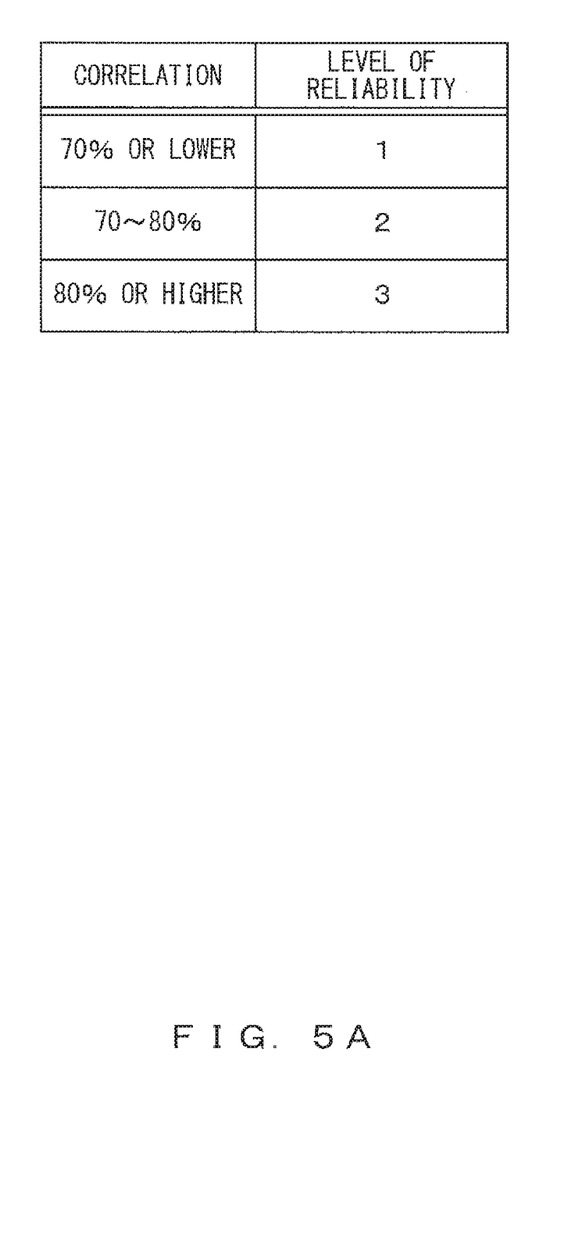
FIG. 5A illustrates an example of a reliability table.
Figure 5B:
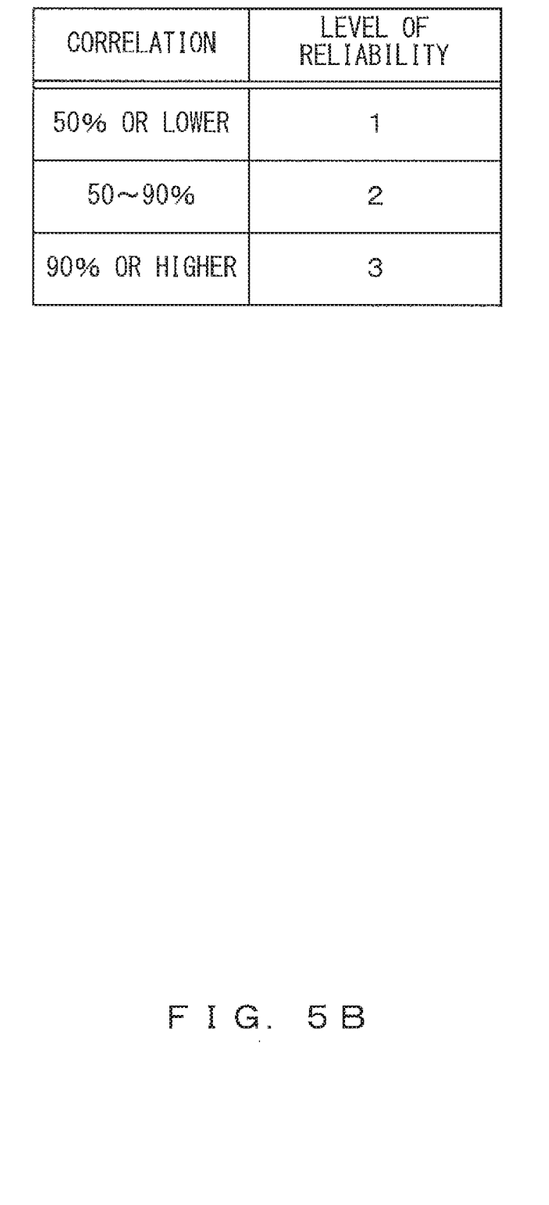
FIG. 5B illustrates an example of a reliability table.

Examples of the generated reliability data will be described. FIG. 5A and FIG. 5B illustrate generation tables of the reliability data 530. It is assumed that the generation tables are provided in association with the respective sensors. For example, FIG. 5A illustrates the generation table of the reliability data 531 of sensor a and FIG. 5B illustrates the generation table of the reliability data 532 of sensor b. The levels of the reliabilities correspond to reliability data. While the levels of reliabilities are described in three steps in this example, the levels may be described in four or more steps. Also, different numbers of steps may be provided depending upon the sensors.

When the correlation of sensor a is measured to be 75%, level 2 is generated as the reliability of sensor a on the basis of the generation table illustrated in FIG. 5A. When the correlation of sensor b is measured to be 95%, level 3 is generated as the reliability of sensor b on the basis of the generation table illustrated in FIG. 5B.

The evaluation generator 520 stores the generated reliability data 530 in the non-volatile memory 114 (step S16). The levels of the reliabilities generated on the basis of the generation tables are stored as the reliability data 530.

Next, explanations will be given for an alert determination process in a case when an abnormality occurred in biological information during the monitoring of a patient. An alert determination process is performed by the alert determinator 600. Two embodiments (first and second embodiments) will be explained for an alert determination process.

First Embodiment

Figure 6:
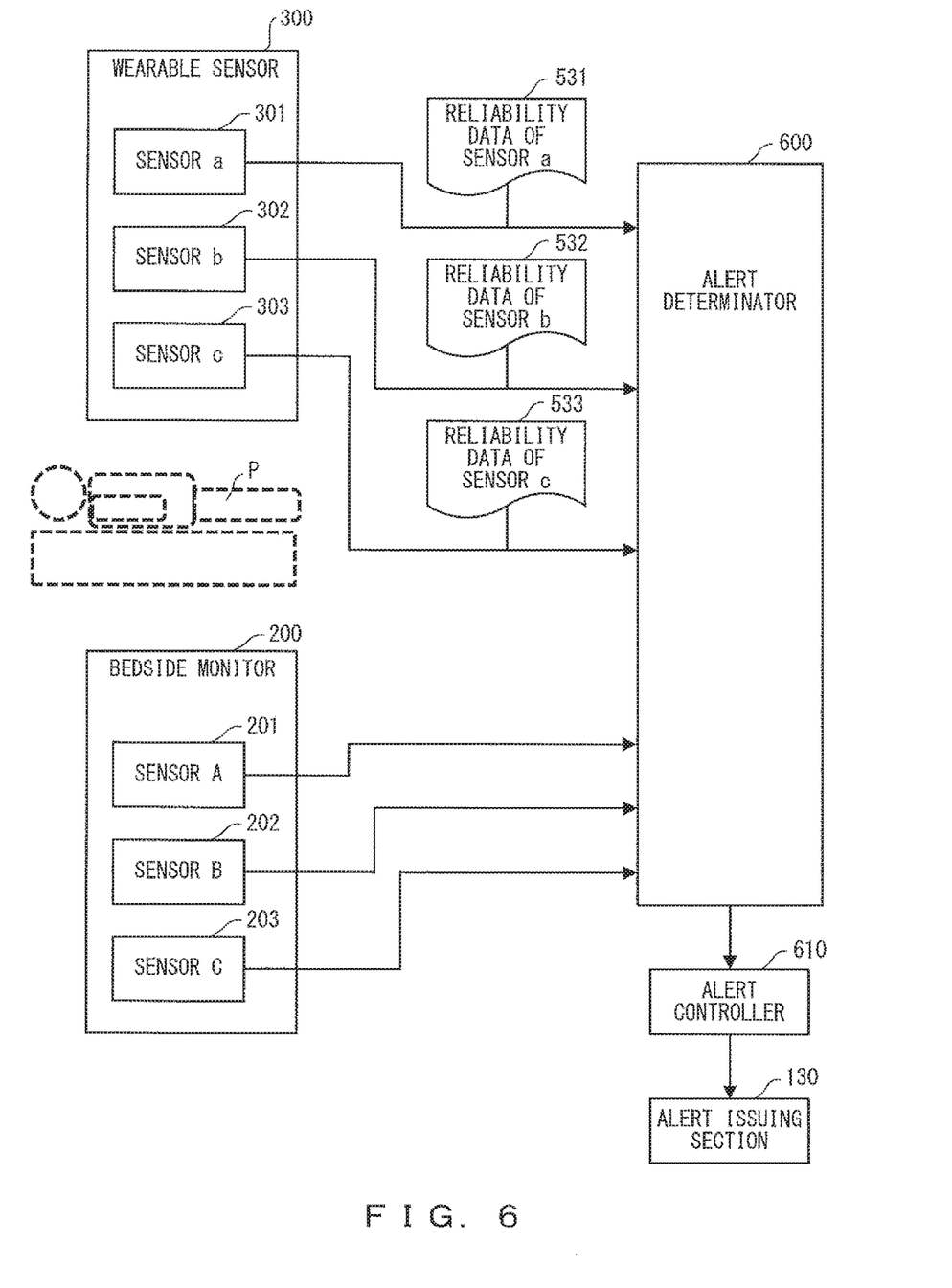
FIG. 6 is a block diagram explaining the first embodiment of an alert determination process.
Figure 7:
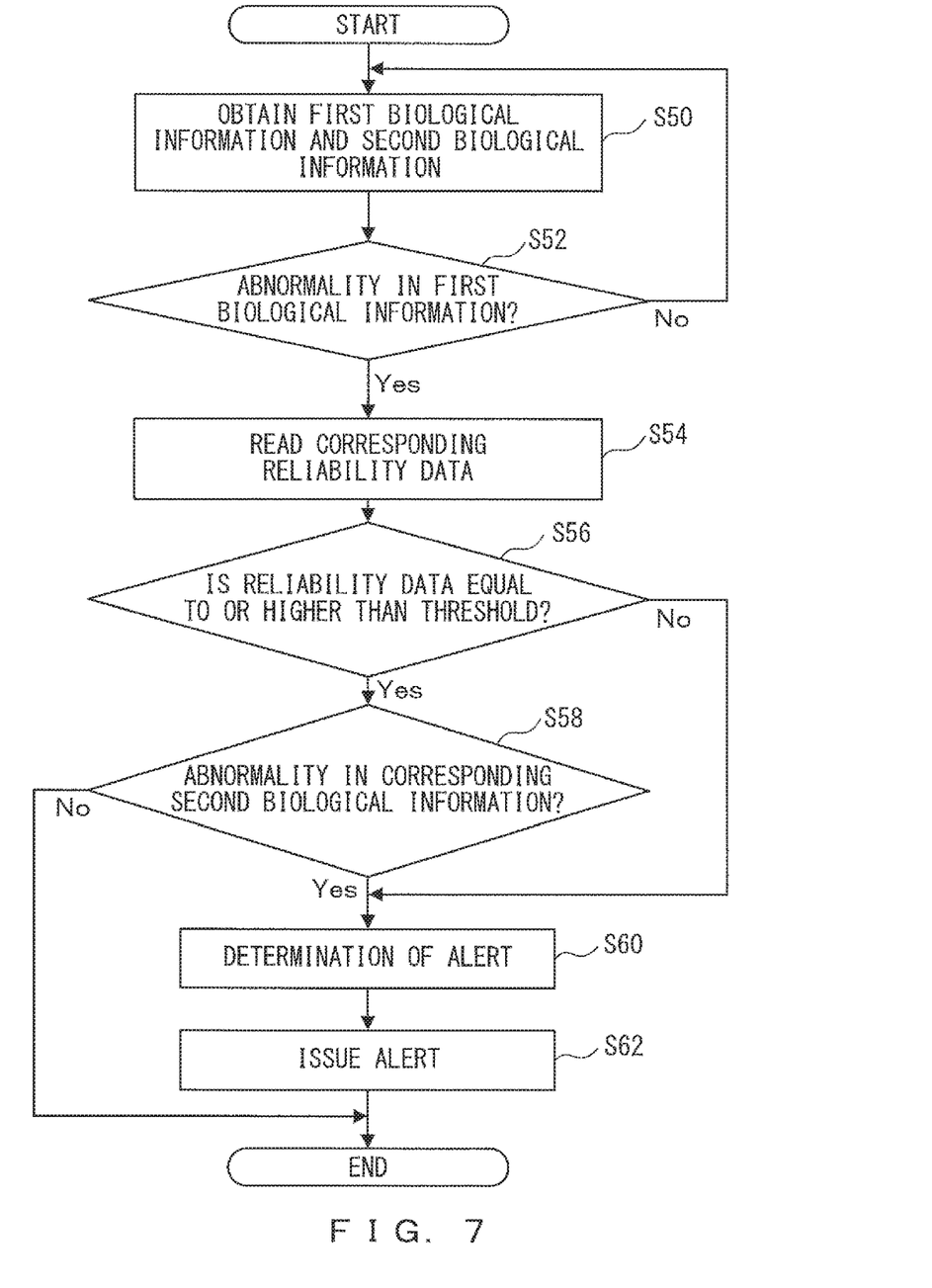
FIG. 7 is a flowchart explaining the sequence of the first embodiment of an alert determination process.

FIG. 6 is a block diagram explaining the first embodiment of an alert determination process. FIG. 7 is a flowchart explaining the sequence of the first embodiment of an alert determination process.

As illustrated in FIG. 6, the alert determinator 600 obtains first biological information from sensor A, sensor B and sensor C, and obtains second biological information from sensor a, sensor b and sensor c. The alert determinator 600 uses the first biological information and second biological information to determine whether to issue an alert about an abnormality under a condition corresponding to the reliability data. When the alert determinator 600 determines that an alert is to be issued, the alert controller 610 controls the alert issuing section 130 and makes it generate for example an alarm sound.

In FIG. 7, the alert determinator 600 obtains the first biological information and second biological information (step S50). The alert determinator 600 determines whether an abnormality occurred in any of the pieces of first biological information (step S52). The alert determinator 600 compares each value of the first biological information and the corresponding normality scope data 540, and determines that an abnormality occurred when any of the pieces of the first biological information is out of the corresponding normality scope data 540.

When it is determined that an abnormality occurred in none of the pieces of the first biological information (NO in step S52), the alert determinator 600 returns to step S50.

When it is determined that an abnormality occurred in any of the pieces of the first biological information (YES in step S52), the alert determinator 600 reads the reliability data 530 of the wearable sensor 300 corresponding to the first biological information in which the abnormality occurred (step S54). For example, when an abnormality occurred in the data of sensor A 201, the reliability data 531 of sensor a 301 is read.

The alert determinator 600 determines whether the reliability data 530 is equal to or greater than a threshold (step S56). In the example of the reliabilities (levels 1 through 3) as explained in FIG. 5A and FIG. 5B, if the reliability of a corresponding sensor is level 3 in a case when the threshold is 2, the determination result is YES. Note that the threshold is stored in the non-volatile memory 114.

When it is determined that the reliability data 530 is not equal to or greater than the threshold (NO in step S56), the alert determinator 600 makes a determination of an alert (step S60). The alert controller 610 causes an alarm sound to be generated (step S62). Specifically, the alert determinator 600 determines that an alert is to be issued by adopting the result of the bedside monitor 200 without taking the corresponding second biological information into consideration because the reliability of the wearable sensor 300 is low.

The explanation returns to step S56. When it is determined that the reliability data 530 is equal to or greater than the threshold (YES in step S56), the alert determinator 600 determines whether an abnormality was detected in the corresponding second biological information as well (step S58).

When it is determined that an abnormality was not detected in the corresponding second biological information (NO in step S58), the alert determinator 600 determines not to issue an alert and terminates the present process. This is because an abnormality is not detected in the highly reliable wearable sensor 300, leading to an estimation that a sensor of the bedside monitor 200 malfunctioned.

When it is determined that an abnormality was detected in the corresponding second biological information (YES in step S58), the alert determinator 600 determines that an alert is to be issued (step S60). The alert controller 610 causes an alarm sound to be generated (step S62). Because the reliability of the wearable sensor 300 is high, the alert determinator 600 determines that an abnormality occurred by also taking the information from the bedside monitor 200 into consideration.

Note that the alert determinator 600 may set an alarm sound issued when the determination result is YES in step S58 to be louder than an alarm sound issued when the determination result is NO in step S56. This is because an abnormality is more likely to have occurred in a case when the determination result is YES in step S58 than in a case when the determination result is NO in step S56.

Second Embodiment

Figure 8:
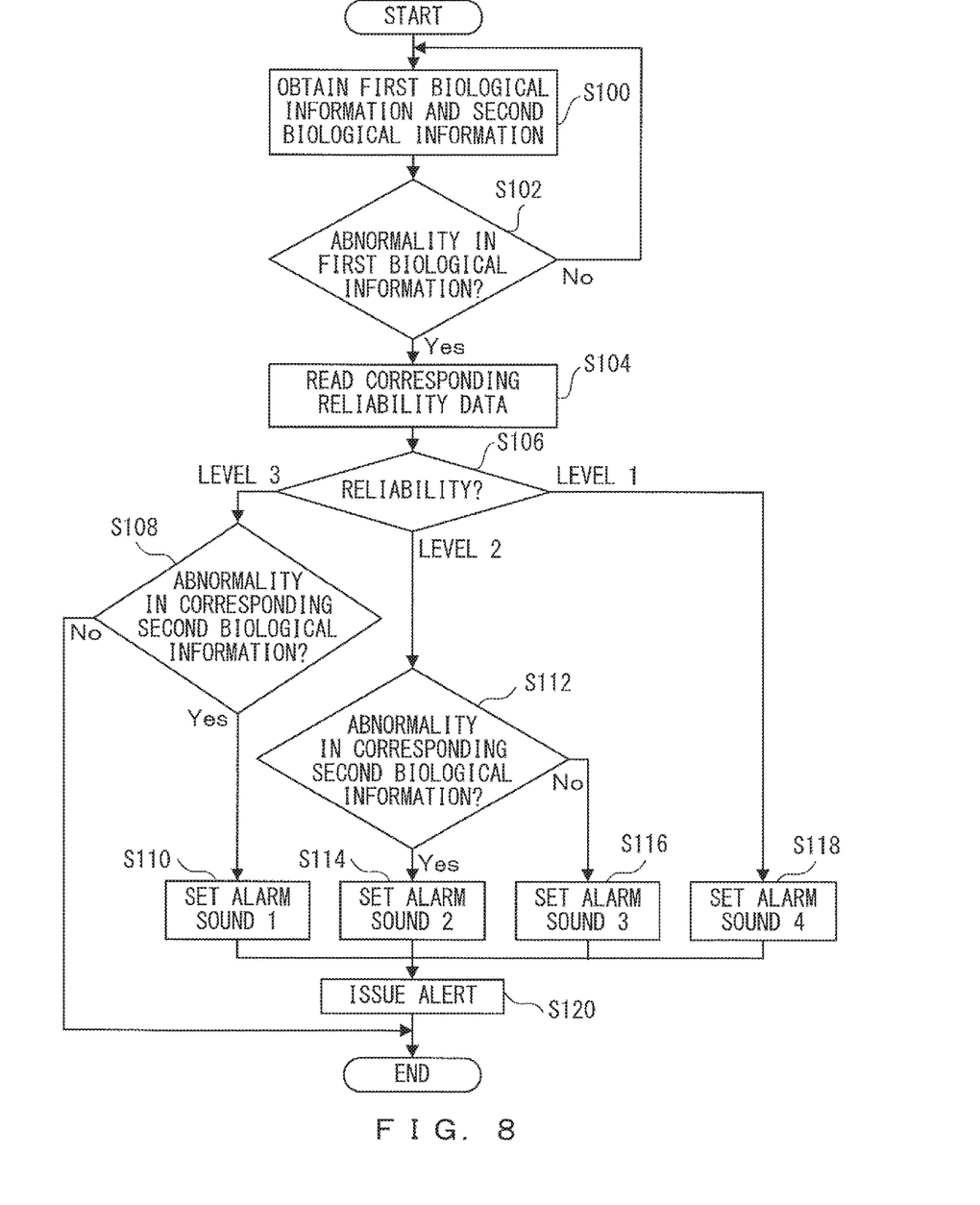
FIG. 8 is a flowchart explaining the sequence of an alert determination process according to the second embodiment.

FIG. 8 is a flowchart explaining the sequence of an alert determination process according to the second embodiment. The block diagram of an alert determination process according to the second embodiment is identical to the block diagram (FIG. 6) according to the first embodiment, and thus explanations thereof will be omitted.

The alert determinator 600 obtains first biological information and second biological information (step S100). The alert determinator 600 determines whether an abnormality occurred in any of the pieces of the first biological information (step S102). The alert determinator 600 compares each value of the first biological information and the corresponding normality scope data 540, and determines that an abnormality occurred when any of the pieces of the first biological information is out of the corresponding normality scope data 540.

When it is determined that an abnormality occurred in none of the pieces of the first biological information (NO in step S102), the alert determinator 600 returns to step S100.

When it is determined that an abnormality occurred in any of the pieces of the first biological information (YES in step S102), the alert determinator 600 reads the reliability data 530 of the wearable sensor 300 corresponding to the first biological information in which the abnormality occurred (step S104).

The alert determinator 600 selects a process, depending upon the read reliability. When it is determined that the corresponding reliability is level 3 in step S106, the alert determinator 600 determines whether an abnormality occurred in the corresponding second biological information (step S108). Level 3 is a high reliability. For example, when an abnormality occurred in data of sensor A, the process in step S108 is performed if the reliability data 531 of sensor a is level 3. In step S108, whether an abnormality occurred in data of sensor a is determined.

When it is determined that an abnormality did not occur in the corresponding second biological information (NO in step S108), the alert determinator 600 terminates the process without issuing an alert. This is because an abnormality is not detected in the highly reliable wearable sensor 300, leading to an estimation that a sensor of the bedside monitor 200 malfunctioned.

When it is determined that an abnormality occurred in the corresponding second biological information (YES in step S108), the alert determinator 600 sets alarm sound 1 (step S110). The alert controller 610 causes an alert to be issued in the form of alarm sound 1 (step S120). The alert controller 610 sets different sounds as alarm sounds depending upon the likelihood of abnormalities. Alarm sound 1 is the sound that draws attention the most, and the sound becomes more moderate as the number becomes greater. One or two of the volume, the pitch, the tone, the length, and the rhythm of the sound may be combined so as to change alarm sounds 1 through 4. Because an abnormality was detected in the highly reliable wearable sensor 300, the occurrence of an abnormality is determined by also taking the information from the bedside monitor 200 into consideration.

The explanation returns to step S106. When it is determined that the reliability of the corresponding second biological information in step S106 is level 2, the alert determinator 600 determines whether an abnormality occurred in the corresponding second biological information (step S112).

The alert determinator 600 determines that an abnormality occurred in the corresponding second biological information (YES in step S112), and sets alarm sound 2 (step S114). The alert controller 610 causes an alert to be issued in the form of alarm sound 2 (step S120). Because an abnormality was detected in the highly reliable wearable sensor 300, the occurrence of an abnormality is determined by also taking the information from the bedside monitor 200 into consideration. However, the reliability of the second biological information is slightly lower than in step S110, and accordingly alarm sound 2, which has for example a volume slightly lower than alarm sound 1 in step S110, is set.

The alert determinator 600 determines that an abnormality did not occur in the corresponding second biological information (NO in step S112), and sets alarm sound 3 (step S116). The alert controller 610 causes an alert to be issued in the form of alarm sound 3 (step S120). Because the reliability of the second biological information is slightly lower than in step S114, alarm sound 3 is set, which has for example a volume further lower than in step S114.

Explanation returns to step S106. When it is determined that the reliability of the corresponding second biological information is level 1 in step S106, the alert determinator 600 sets alarm sound 4 (step S118). The alert controller 610 causes an alert to be issued in the form of alarm sound 4 (step S120). Because the reliability of the corresponding wearable sensor 300 is low, results of the bedside monitor alone are adopted.

<Effects>

According to the present embodiments, second biological information (data of the wearable sensor 300) is appropriately combined with first biological information (sensor data of the bedside monitor 200), which is the main biological information, making it possible to prevent the issuance of false alerts (false issuance) while preventing oversights of the occurrence of abnormalities. Prevention of false alerts can reduce burdens on medical staff members.

Also, by combining the second measurement apparatus (the wearable sensor 300) based on sensors having sensitivities and types different from the sensors of the first measurement apparatus (the bedside monitor 200), the likelihood of errors occurring at the same time can be reduced and issuance of false alerts can be prevented.

Because second biological information is used for a determination of an alert in a case when the reliability of the second biological information is high, it is possible to prevent false issuance from being caused by second biological information that is of a low reliability. The higher the reliability of second biological information, the louder the alarm sound is set to be. This makes it possible for medical staff members who hear an alarm sound to decide the level of the importance or urgency by an aspect of an alarm sound (for example, the volume of the sound, the pitch of the sound and the frequency of the sound in a pulse form).

Variation Example 1

While differences in levels between alerts are utilized as aspects of alarm sounds in the second embodiment, visual effects such as the display or the blinking of an LED (color, interval of blinking) in tablets carried by doctors or nurses may be presented in accordance with the levels of alerts. The alert controller 610 includes a visual effect displaying section that displays visual effects.

Variation Example 2

The second measurement apparatus is not limited to a wearable sensor. This is because any sensor can be used as long as it can verify the accuracy of a bedside monitor. The second measurement apparatus does not have to be a wearable sensor as long as the second measurement apparatus is a sensor of a type and scheme different from those of sensors of a bedside monitor.

Note that the present invention is not directly limited to the above embodiments, but can be embodied with modifications on the constituents without departing from the spirit of the present invention in embodying phases. Also, various inventions can be formed by an appropriate combination of a plurality of constituents disclosed in the above embodiments. For example, all the constituents disclosed in the embodiments may be combined appropriately. Further, constituents may be combined appropriately across different embodiments. As a matter of course, various modifications and applications are possible without departing from the spirit of the invention.

NUMERALS

1 MEDICAL MONITORING SYSTEM
100 MEDICAL MONITORING APPARATUS
110 CPU
112 TEMPORARY MEMORY
114 NON-VOLATILE MEMORY
116 INPUT/OUTPUT I/F
118 BUS
120 DISPLAY UNIT
130 ALERT ISSUING SECTION
140 INFORMATION PROCESSING APPARATUS
200 BEDSIDE MONITOR
201 SENSOR A
202 SENSOR B
203 SENSOR C
300 WEARABLE SENSOR
301 SENSOR a
302 SENSOR b
303 SENSOR c
400 MONITORING CONTROLLER
500 RELIABILITY EVALUATOR
510 CORRELATION MEASUREMENT SECTION
520 EVALUATION GENERATOR
530 RELIABILITY DATA
600 ALERT DETERMINATOR
610 ALERT CONTROLLER

What is claimed is:

1. A medical monitoring apparatus that monitors a status of a patient according to biological information of the patient, the medical monitoring apparatus comprising:
    a reliability evaluator configured to obtain first biological information measured by a first measurement apparatus together with second biological information measured by a second measurement apparatus, and to evaluate a reliability of the second biological information according to a correlation between the first biological information and the second biological information, the first biological information and the second biological information belonging to an identical measurement item and the second measurement apparatus having accuracy or sensitivity lower than accuracy or sensitivity of the first measurement apparatus; and
    an alert determinator configured to determine, using the first biological information and the second biological information, whether to issue an alert about an abnormality of the patient under a condition that depends on the reliability;
    wherein in a case where the reliability evaluator has determined that the reliability of the second biological information is high, the alert determinator determines that an alert is to be issued when both the first biological information and the second biological information indicate an abnormality, and
    in a case where the reliability evaluator has determined that the reliability of the second biological information is low, the alert determinator determines that an alert is to be issued when the first biological information indicates an abnormality.

2. The medical monitoring apparatus according to claim 1, wherein
    the biological information of the patient measured by the first measurement apparatus and the biological information of the patient measured by the second measurement apparatus are at least any one of a body temperature, an electrocardiogram, a heart rate, brain waves, and a blood pressure.

3. The medical monitoring apparatus according to claim 1, wherein
    the first measurement apparatus is a bedside monitor, and the second measurement apparatus is a wearable sensor attached directly to the patient.

4. The medical monitoring apparatus according to claim 1, wherein
the reliability evaluator repeatedly calculates the correlation at predetermined timings during the monitoring, and evaluates the reliability by comparing the calculated correlation with a predetermined threshold.

5. The medical monitoring apparatus according to claim 1, wherein
the reliability evaluator sets a level for the reliability according to the correlation.

6. The medical monitoring apparatus according to claim 5, comprising:
an alert controller configured to control an alert mode, wherein the alert controller changes the alert mode in accordance with the set level of the reliability.

7. The medical monitoring apparatus according to claim 6, comprising:
a speaker configured to generate an alarm sound;
wherein the alert controller changes the mode of the alarm sound in accordance with the set level of the reliability.

8. The medical monitoring apparatus according to claim 7, wherein
the alarm controller makes a change in at least one of alarms mode i.e. volume, tone, duration of cyclic alarm, as the level of the reliability changes.

9. The medical monitoring apparatus according to claim 6, comprising:
a visual effect displaying section configured to display an visual effect,
wherein the alert controller changes the mode of the visual effect in accordance with the set level of the reliability.

10. A medical monitoring apparatus that includes a controller that determines whether to issue an alarm about an abnormality of a patient according to biological information of the patient, wherein
the controller obtains first biological information measured by a first measurement apparatus together with second biological information measured by a second measurement apparatus, and evaluates a correlation between the first biological information and second biological information, the first biological information and the second biological information belonging to an identical measurement item and the second measurement apparatus having accuracy or sensitivity lower than accuracy or sensitivity of the first measurement apparatus,
the controller determines a level of a reliability of the second biological information according to the correlation, and stores the determined level of the reliability in a storage, and
the controller determines, using the first biological information and the second biological information, whether to issue an alert about an abnormality of the patient under a condition that depends on the level of the reliability stored in the storage;
wherein in a case where the reliability of the second biological information is determined to be high, the controller determines that an alert is to be issued when both the first biological information and the second biological information indicate an abnormality, and
in a case where the reliability of the second biological information is determined to be low, the controller determines that an alert is to be issued when the first biological information indicates an abnormality.

11. A non-transitory computer-readable medium having stored therein a program for causing a computer to perform a process comprising:
performing an alarm method to determine whether to issue an alert about an abnormality of a patient according to biological information of the patient;
obtaining first biological information measured by a first measurement apparatus together with second biological information measured by a second measurement apparatus, the first biological information and the second biological information belonging to an identical measurement item and the second measurement apparatus having accuracy or sensitivity lower than accuracy or sensitivity of the first measurement apparatus;
evaluating a reliability of the second biological information according to a correlation between the first biological information and the second biological information; and
determining, using the first biological information and the second biological information, whether to issue an alert about an abnormality of the patient under a condition that depends on the reliability;
wherein in a case where the reliability of the second biological information is determined to be high, an alert is issued when both the first biological information and the second biological information indicate an abnormality, and
in a case where the reliability of the second biological information is determined to be low, an alert is issued when the first biological information indicates an abnormality.

* * * * *